United States Patent [19]

Connelly

[11] Patent Number: 4,906,567

[45] Date of Patent: Mar. 6, 1990

[54] NON-IMMUNOCHEMICAL BINDING OF LIPOPOLYSACCHARIDES AND SANDWICH ASSAYS THEREFOR

[75] Inventor: Mark C. Connelly, New Castle, Del.

[73] Assignee: E. I. Dupont De Nemours and Company, Wilmington, Del.

[21] Appl. No.: 11,327

[22] Filed: Jan. 21, 1987

[51] Int. Cl.$^4$ .................. G01N 33/579; G01N 33/569
[52] U.S. Cl. .......................................... 435/7; 436/502; 436/518; 436/827; 436/511; 536/127; 435/264
[58] Field of Search ............... 436/501, 502, 518, 827, 436/815, 511; 435/7, 264; 536/127

[56] References Cited

U.S. PATENT DOCUMENTS

| | | | |
|---|---|---|---|
| 3,915,805 | 10/1975 | Levin | 436/502 |
| 4,134,792 | 1/1979 | Boguslaski et al. | 435/4 |
| 4,683,196 | 7/1987 | McLaughlin | 435/7 |

OTHER PUBLICATIONS

"Endotoxin Contamination of Enzyme Conjugates Used in Enzyme-Linked Immunosorbent Assays", R. E. Bryant et al., *Journal of Clinical Microbiology* 17(6); 1050–1053;1983.

"Immobilized Enzymes", O. Zaborsky, p. 75,1973, CRC Press.

"Removal of Gram-Negative Endotoxin from Solutions by Affinity Chromatography", A. C. Issekutz, *Journal of Immunological Methods* 61;275–281; 1983.

*Primary Examiner*—Esther M. Kepplinger
*Attorney, Agent, or Firm*—George A. Frank

[57] ABSTRACT

Sandwich assays for detecting and identifying lipopolysaccharides of gram negative bacteria utilizing immobilized lipopolysaccharide binding proteins and labelled detection reagents are provided. The active supports are also useful in removing LPS from biomedical and cosmetic preparations.

8 Claims, No Drawings

NON-IMMUNOCHEMICAL BINDING OF LIPOPOLYSACCHARIDES AND SANDWICH ASSAYS THEREFOR

TECHNICAL FIELD

This invention is related to the field of specific binding assays and specifically to sandwich assays for detecting lipopolysaccharides (LPS) of gram negative bacteria and to the removal of LPS from materials for biomedical or cosmetic applications.

BACKGROUND ART

Gram negative bacteria, and some protozoa, are known to produce a cell surface glycolipid substance called lipopolysaccharide (LPS). Lipopolysaccharide is not a component of either human tissues or gram positive bacteria; thus, it is a marker specific to gram negative bacteria and a few pathogenic protozoa. In addition, at an estimated one million molecules per cell, it is the most abundant component on the cell surface of gram negative bacteria. All lipopolysaccharides possess two functionally distinct regions of structure: a fatty portion called "lipid A" and a carbohydrate section containing as few as 3 and up to as many as 350 and sometimes more sugar residues.

The carbohydrate portion of LPS may itself be divided into two structural entities: the core, generally composed of 8 to 11 sugar residues shared by all the members of a particular genus, and the O-side chain which is unique to a given species or a particular antigenic subgroup of a given speices. The majority of the antigenic sites on LPS are localized in the carbohydrates of the core and O-side chain. Antibodies specific for each portion of the LPS structure have been developed. An antibody specific for the core region of Salmonella LPS will react with Salmonella LPS regardless of the species from which it was derived, but will not react with LPS from other bacteria such as various Escherichia species. Antibodies specific for the O-side chain of a particular species of Salmonella will only react with members of that species and will not react with LPS from other species of Salmonella or other gram negative bacteria.

The lipid A portion of LPS possesses the majority of the physiological activity of LPS. Two such activities of lipid A are particularly important clinically. They are its ability to induce fever (pyrogenicity) and its ability to induce generalized vascular collapse (septic or endotoxic shock). Although improvements in treatment have resulted in better prognoses for many victims of shock, those suffering from endotoxic shock still have a mortality rate of 70 to 80% [Robins, Cotran, Pathologic Basis of Disease, W. B. Saunders Co., Philadelphia, PA, 140 (1979)]. Lipid A is a potent inducer of endotoxic shock. Clinical symptoms in humans typically result from levels as low as 3 to 4 pg of lipid A in LPS/mL of blood [Elin, et al., Bacterial Endotoxins: Structure, Biomedical Significance, and Detection with the Limulus Amebocyte Lysate Test, Ed. Cate et al., Alan R. Liss, Inc., New York, Pages 307-324 (1985)]. For a discussion of the Limulus amebocyte lysate test, see below. Thus, the structure of LPS can be summarized as having a carbohydrate region well suited to antigenic analysis and organism identification, and a highly conserved lipid A section possessing poor antigenic properties but potent physiological activity.

In addition to endotoxic shock, gram negative bacteria are frequently the etiologic agent of meningitis, urinary track infections, anaerobic abscesses, urethritis, food poisoning, and other human or veterinary ailments. For all of these conditions, there is a need to make an accurate and timely diagnosis so as to control the further spread of infection and to insure proper treatment. Generally, samples taken from a patient must be cultured for between 18 and 120 hours before a definitive diagnosis can be made. Often, physicians cannot wait for culture results before beginning patient treatment. This delay between the start of treatment and the receipt of culture results means that culture results serve to confirm or refute a presumptive diagnosis but do not influence the initial choice of patient therapy. The high cost of physician's malpractice insurance and the cost containment measures imposed by governmental diagnosis related groups (DRG's) has placed the practice of medicine under increased pressure to eliminate treatment with unncessary and potentially harmful agents. Thus, there is a need for a test that is sensitive, specific, and can provide information on which to make a diagnosis, within a time frame that will help in the initial choice of therapeutic agents. The primary need is to detect the presence of LPS produced by gram negative bacteria followed by genus/species identification.

One approach to meeting this need has been to develop immunoassays to detect antigens in clinical samples. Although ideally one would want to utilize an antibody to lipid A because of its highly conserved structure, no antibody with sufficiently high affinity and crossreactivity to be useful in an immunoassay has been found. The carbohydrate O-side chains contain many copies of the antigenic sites and can therefore bind many antibody molecules. This makes capturing and detecting these antigens in a sandwich immunoassay easy and very sensitive. However, O-side chains are restricted in their utility because of their extreme antigenic heterogeneity among microbial species. The carbohydrates of the inner core might be of greater utility due to their more conserved structure but generally the core structure is only capable of binding a single antibody making a sandwich immunoassay practically impossible.

One of the oldest tests for monitoring endotoxin (LPS) contamination is the rabbit pyrogenecity test. A sample of the material to be tested is serially diluted and aliquots of each dilution are injected into rabbits. The rabbit's temperature is then monitored. If the rabbit's temperature becomes elevated, the sample is deemed to be contaminated. An estimate of the quantity of LPS contamination is obtained as the reciprocal of the dilution at which no significant increase in temperature is observed in the rabbits. This assay is imprecise, requires large numbers of animals, and is of little use as a diagnostic procedure because it does not provide any information regarding the nature of the LPS or the organism from which it is derived. It is also expensive for industrial manufacturers to have to perform routinely, and has a limit of detection in the range of 100 ng LPS/mL liquid.

A rapid and sensitive test for the presence of LPS is the Limulus amebocyte lysate (LAL) test based on the work of Levin and Bang [Tai et al., J. Biol. Chem., Volume 252, 2178-2181 (1977)]. The horseshoe crab (*Limulus polyphemus*) possesses a primitive but effective defense against gram negative organisms. The LPS of the invading organism stimulates a series of reactions that culminates in the formation of a clot around the intruder. The enzymes and coagulogen proteins needed to form the clot are located in intracellular granules of the amebocytes that circulate in the blood of the horseshoe crab. When these amebocytes are separated from the blood by centrifugation, washed, and then lysed, the result is a clear and fluid cell lysate. In the LAL test, when this cell lysate is exposed to even picogram amounts of LPS, it becomes turbid and forms a gelatinous clot.

An improvement over the LAL test described above is the LAL chromogenic assay. This assay is based on the fact that gelation in the LAL test is the result of the action of a cascade of serine proteases. These proteases can be monitored directly in a non-LAL coagulation test format by adding a chromogenic substrate, such as those used in monitoring mammalian blood clotting enzymes, to the reaction mixture and observing color formation. Generally, this assay shows greater sensitivity than the LAL coagulation test and can be monitored using an analytical instrument rather than human observer.

Although both of the above LAL-based tests are extremely sensitive to LPS, and only LPS, and, therefore, to the presence of gram negative bacteria, they provide no information regarding the nature of the LPS or the organism from which the LPS is derived. In fact, the extraordinary sensitivity of Limulus amebocyte lysate to LPS limits its utility in the LAL test to those samples which contain the LPS of interest or to those samples in which the mere presence of any LPS is of interest. For many clinical specimens, for example a throat or rectal swab, commensal gram negative organisms would be present and, therefore, a positive Limulus lysate test would not necessarily indicate the presence of a potential pathogen. Furthermore, the Limulus lysate test cannot be performed on any sample that contains either a serine protease or an inhibitor of a serine protease, such as those involved in platelet aggregation and blood clotting, because such enzymes interfere with clot formation.

In an effort to determine whether a commercially available enzyme preparation was contaminated with endotoxin, Bryant et al. [J. Clin. Microbiol., Volume 17, 1050 (1983)] reported immobilizing Limulus amebocyte lysate on a microtiter plate. The lysate was immobilized by adsorption to the polystyrene wells using a standard carbonate-bicarbonate buffer, pH 9.6. The authors presumed that if enzyme was retained in LAL-coated wells, but not in blank, uncoated wells, the retention could only have been the result of the capture of complex formed between LPS contamination present in the sample and the enzyme. Since enzyme was, in fact, found to have been retained, the authors assumed LPS contamination.

LPS binding proteins are also known to be isolated from amebocytes present in the blood of *Tachypleus tridentatus, Tachypleus gigas* and *Carcinoscorpius rotundicauda*. Lysates from these amebocytes can substitute for Limulus amebocyte lysates [Nakamura et al., Biochemica et Biophysica Acta, Volume 707, 217-225 (1982)].

The ubiquitous presence of gram negative bacteria in the environment also presents a challenge to manufacturers of biomedical supplies and cosmetics. The potency and clinical consequences of LPS contamination make it necessary that such products be certifiably free of LPS. This need has created a demand for fast, reliable, and inexpensive assays for the detection of endotoxins. There also exists a need to remove LPS from contaminated products.

DISCLOSURE OF THE INVENTION

The sandwich assay of this invention for detecting lipopolysaccharides comprises the steps of:
(A) immobilizing a capture reagent to form an active support consisting essentially of
 (i) a water insoluble support; and
 (ii) lipopolysaccharide binding proteins bound to said support;
(B) contacting a sample containing or suspected of containing lipopolysaccharides with said active support;
(C) contacting the active support-LPS complex formed in step (B) with a labelled detection reagent; and
(D) detecting either the bound or unbound label.

The method of this invention for removing lipopolysaccharides from a sample comprises the steps of:
(A) immobilizizing a capture reagent to form an active support consisting essentially of
 (i) a water insoluble support; and
 (ii) lipopolysaccharide binding proteins bound to said support;
(B) contacting a sample containing or suspected of containing the lipopolysaccharide with the active support; and
(C) separating the LPS bound to the active support from the sample.

Binding lipopolysaccharide binding proteins to a support is carried out by adsorbing the LPS binding proteins to a solid support at a pH of less than about 9.0.

DESCRIPTION OF THE INVENTION

This invention takes advantage of the surprising finding that when a capture reagent such as Limulus amebocyte lysate (LAL) is immobilized onto a solid support, not only is the LAL still capable of binding LPS but the bound LPS is antigenically intact and is still accessible to antibodies. This means that the broad reactivity toward LPS of the components found in Limulus and Tachypleus amebocyte lysates can be used as a generic means of capturing and immobilizing LPS. This allows either the detection of the presence of LPS or antigenic analysis. The method of this invention is capable of capturing many different kinds of LPS for those applications where it is important to detect the presence of any kind of LPS regardless of its type. Furthermore, the method of this invention is especially useful in analyzing samples where it is necessary to ignore the LPS from irrelevant or commensal organisms while maintaining the ability to detect and specifically identify particular LPS species from pathogenic gram negative bacteria. Still further, this invention is not affected by either serine proteases or inhibitors of serine proteases, and can be used with such samples. Also, the method of this invention is capable of providing organism specific identification of pathogens in less than 30 minutes. This could be important information delivered in a timely manner to help physicians in choosing initial therapeutic agents.

The lipopolysaccharide (LPS) binding proteins from various organisms such as of *Limulus polyphemus, Tachypleus tridentatus, Carcinoscorpius rotundicauda* and *Tachypleus gigas* can be used as specific, non-immunologic capture reagents to bind LPS to a solid support. These capture reagents can be in the form of the lysate of the amebocytes from these organisms or can be specific proteins from such lysates. It is expected that Factor C and Anti-LPS Factor will be preferable. These are the two proteins within the lysate currently recognized as having specific LPS binding activity. It is possible that the LPS binding capacity and specific activity of the support can be increased by using purified LPS binding proteins. Alternatively, pure LPS binding proteins can be produced using recombinant DNA technology.

The supports useful in the method of this invention can take many forms and be constructed of many different materials. Preferred supports are generally solids, most preferably polymeric materials such as polystyrene. The shape of the support is not critical and will generally be determined by the intended application. The surface area of the support can also affect assay performance. The supports can be porous or non-porous. Some convenient forms of support are the wells of microtiter plates, small spheres, and sub-micron sized irregular particles.

The LPS binding proteins can be bound to the support in a number of ways. For purposes of discussion, support to which LPS binding protein had been bound will be referred to as active supports. It is generally preferred to adsorb the binding proteins to the surface of the support but covalent attachment can also be used. Homobifunctional agents, such as glutaraldehyde, or heterobifunctional agents can be used. Regardless of the mode of binding chosen, the pH of the buffers employed in the coupling procedure should be maintained below about 9, preferably below about 8 and most preferably near 7. Buffers with pH values near neutral are preferred because higher pH buffers destroy substantially all LPS binding activity of the LPS binding proteins. This is in direct contrast to the report of Bryant et al., supra, where binding was reported to be accomplished at pH 9.6. Wells of a microtiter plate were coated with LAL in either pH 7.4 PBS or pH 9.6 carbonate and incubated at room temperature for 2 hours. Except for the differences in the pH of the coating buffer, all wells were treated with *N. gonorrhoeae* cells and a monoclonal antibody-enzyme conjugate in an identical manner in the assay. Wells containing only LAL in pH 7.4 PBS showed background optical density (OD) at 630 nm equal to 0.110±0.014 versus an OD at 630 nm equal to 0.438±0.017 for assay test wells (signal to noise ratio=4.0). In contrast, wells containing only LAL in pH 9.6 carbonate buffer showed background OD at 630 nm equal to 0.118±0.013 versus an OD at 630 nm equal to 0.123±0.020 for the assay test wells (signal to noise ratio=1.0). The results indicated that the sandwich assay of this invention should utilize buffer for the preparation of the active support at or below about pH=9.

It is important that all reagents, including buffers, and equipment used during binding of the binding protein to the support be substantially free of contaminating LPS. This is especially true when crude lysate is being bound to the solid support. A small amount of LPS contamination can be tolerated after the LPS binding proteins have been immobilized since reagent coagulation is no longer a problem. LPS contamination, nevertheless, is to be avoided. Extraneous LPS introduced during coupling and washing steps can reduce the binding capacity of the active support and can also cause a false positive result if the contaminating LPS is reactive with the labeled detection reagent. To insure that the reagents utilized during LPS assay are LPS free, one needs to utilize LPS-free water which can be obtained as pyrogen-free water or purified by known methods. It is considered advisable to test the water and reagents periodically with the LAL coagulation assay to insure that they are LPS free.

It is also important that the buffers and reagents be substantially free of surfactants. Surfactants such as polyoxyethylene sorbitan monolaurate, polyethylene glycol p-isooctylphenyl ether and deoxycholate have been found to cause, not prevent, high levels of nonspecific binding to immobilized amebocyte lysate. Microtiter plate wells were coated with 100 µl of LAL (236 µg/mL) in PBS. Four wells were washed with PBS and another four with PBS+0.05% polyoxyethylene sorbitan monolaurate. No LPS or bacterial cells were incubated with the immobilized LAL. An anti-*N. gonorrhoeae* LPS-specific monoclonal antibody-enzyme conjugate was incubated in the wells and the wells were washed with either PBS or PBS containing polyoxyethylene sorbitan monolaurate. Substrate was added and the OD at 630 nm was determined. Wells washed with PBS showed an OD=0.093±0.006 whereas wells washed with surfactant-containing PBS showed an OD=0.653±0.042. This is a signal to noise ratio of 7.0. This result could not be due to inapparent growth of *N. gonorrhoeae* in the surfactant-containing PBS followed by specific antibody interaction because *N. gonorrhoeae* is an obligate human pathogen that can only grow within the human body or on specially formulated growth medium. These data are believed to show why Bryant et al. observed apparent retention of binding activity even though high pH buffers were used during adsorption of the LPS binding protein to the support.

After the LPS binding proteins have been bound to the support surface, additional protein binding sites on the support, if any, should be blocked to avoid nonspecific binding of the detection reagents to the support. This can be accomplished by incubating the active support with casein or bovine serum albumin (BSA) solution. Other proteins can be substituted for BSA chosen so as not to interfere with the labelled detection reagent.

After the preparation of the active support is complete, it is contacted with a test sample suspected of containing LPS. The test sample can be any material currently assayed by either of the the LAL assays described above. In addition, the sample can be a physiologic fluid, tissue or excreta from animal or human source. The sample can be contacted with the active support in a broad temperature range, from ambient temperatures on up, with 37° C. being preferred. The sample should remain in contact with the immoblized capture reagent on the active support for a time sufficient to insure capture of substantially all LPS from the sample. This time period will depend upon the size, shape and nature of the support as well as the temperature employed. At ambient temperatures, the time required can range from about 1 hour to about 4 hours, with two hours being preferred. At 37° C., the time can range from about 15 minutes to 2 hours, with 30 minutes being preferred.

After contacting with the test sample, the active support having LPS bound to it can be separated from the unbound material, for example, by washing with surfactant-free buffer. This complex is then incubated with labelled detection reagent. While this sequential addition procedure including a separation step is preferred, other procedures such as eliminating the separation step (the staggered addition procedure) and contacting the active support with the sample and labelled detection reagent substantially simultaneously can be employed. These alternative procedures can reduce the time required to complete the assay, however, assay sensitivity can be reduced. The temperature and time required for the reaction of the labelled detection reagent with the complex can be similar to those used in the first step. Generally, higher temperatures are preferred to diminish the required reaction time. However, the stability of the labelled detection reagent at elevated temperatures needs to be considered in determining optimum reaction temperatures.

The labelled detection reagent is a conjugate of a specific binding protein and a label. The specific binding protein can be an immunoglobulin(s), a lectin(s), or purified LPS binding protein(s) from Limulus or Tachypleus amebocyte lysate. Detection reagents of appropriate specificity or reactivity are chosen to meet the requirements of specific applications and can be mixtures such as based on mixtures of antibodies. Specificity can be limited to individual species, for example, by utilizing an antibody specific for LPS from *Neisseria gonorrhoeae*; or the binding protein can be broadly reactive, as in a purified LPS binding protein. The important consideration is that the detection reagent be specific for a defined set of LPS molecules in order to be able to accomplish the assay goals. For example, to determine whether a fecal sample contains *Neisseria gonorrhoeae*, the detection reagent(s) must be specific for gonococcal LPS. Should the detection reagent also react with LPS from enteric gram negative organisms, it will be unable to distinguish between gonococcal LPS and LPS of the normal flora. However, if the intent is to detect any LPS, irrespective of its origin, or to remove LPS contaminants, then the detection reagent (or reagents) must be broadly reactive and not limited to a subset of LPS species.

The label in the detection reagent conjugate can be any reporter moiety ordinarily utilized in assays. Preferred labels include radioisotopes, enzymes whose activity can be assayed, and fluorescent molecules. The labels can be attached to the specific binding protein, utilizing known chemical methods including direct attachment, attachment through a linker arm or with secondary reagents such as anti-immunoglobulin antibodies or protein A. When secondary reagents are employed, these can be associated with the specific binding protein before or after contacting the specific binding protein with the active support/LPS complex. Examples of these alternatives are the use of an antibody-enzyme conjugate and the use of an antibody first, followed by the attachment of a protein-A-enzyme conjugate.

After incubation, the solid phase can be separated and washed with surfactant-free PBS. Bound detection reagent can then be detected as appropriate for the particular label utilized in the conjugate. Based on the label and method of detection, qualitative or quantitative results can be obtained.

In addition to being useful in specific binding assays, the active support of this invention can be useful in removing LPS from aqueous reagents intended for a variety of other applications such as biomedical or cosmetic applications. The active supports useful in these applications can take different forms from those useful in the specific binding assays, such as higher surface area and greater binding capacity. These active supports can be conveniently constructed in the form of filters, small magnetic particles, etc.

The following examples illustrate the invention.

EXAMPLE 1

Sandwich Assay for Gonococcal LPS

*Neisseria gonorrhoeae* was grown on a chocolate agar plate at 37° C. in a 5% $CO_2$ atmosphere. A pure culture of *N. gonorrhoeae* was transferred to a 1-L shaker flask containing 15 grams of Proteose Peptone number 3 (Difco Laboratories, Detroit, MI), supplemented with 1% of a commercially available nutrient supplement (IsoVitale X Enrichment, BBL Microbiology Systems, Becton Dickerson and Co., Cockeysville, MD) and grown as a broth culture at 37° C. A sample was removed after 18 hours of growth. The sample was serially diluted and inoculated onto chocolate agar plates to determine the number of viable organisms per mL. The rest of the live culture was killed by treatment with heat. The killed cells were harvested by centrifugation, washed with sterile medium, resuspended in a small volume of sterile medium and frozen until needed.

Lyophilized Limulus amebocyte lysate (LAL, Pyrogent, Mallinckrodt, Inc., St. Louis, MO) was reconstituted with LPS-free phosphate buffered saline (PBS) at a protein concentration of 440 µg/mL. 1/5 and 1/10 dilutions of the reconstituted Limulus lysate were prepared in PBS. The pH was 7.2–7.4.

To prepare the active support, the following were added to different wells of a microtiter plate: 100 µL of a 0.5% (w/v) BSA in PBS, and 100 µL Limulus lysate at 440, 88 and 44 µg/mL concentrations. The solutions were allowed to stand in the wells for 2 hours at room temperature. The plate was washed 6 times in PBS. To block nonspecific binding, 200 µL of a 0.5% (w/v) BSA in PBS was added to each of the wells and the plate was allowed to stand at room temperature for 1 hour. The plate was washed 6 times with PBS. All wells then received 100 µL of suspension of *N. gonorrhoeae* at a concentration of $1 \times 10^7$ CFU/mL. The plate was again allowed to stand for 1 hour at room temperature. The plate was washed 6 times with PBS. All wells then received 100 µL of a 1/40 dilution of an *N. gonorrhoeae*-LPS specific monoclonal antibody number 179 (an IgG antibody) conjugated to horseradish peroxidase through a heterobifunctional linking agent, N-succinimidyl-4-(N-maleimidomethyl)cyclohexane-1-carboxylate (SMCC). The monoclonal antibody and its enzyme conjugate were obtained through conventional processes now well known. The plate was allowed to stand for 45 minutes at room temperature. The plate was washed 6 times with PBS. All wells then received 100 µL of freshly prepared chromogenic substrate, 1.5 µM tetramethylbenzidine (TMB) solution and allowed to stand for 15 minutes at room temperature. The optical density was read at 630 nm using a microtiter plate reader (Microplate Reader MR 600, Dynatech, Alexandria, VA) with the reference beam set at 490 nm. The results are a mean of four replicate determinations and are presented in Table 1.

TABLE 1

| DETECTION OF GONOCOCCAL LPS | |
|---|---|
| LAL Added to Well (µg/mL) | Optical Density (at 630 nm) |
| none (0.5% BSA) | 0.017 ± 0.004 |
| 44 | 0.264 ± 0.024 |
| 88 | 0.515 ± 0.043 |
| 440 | 1.123 ± 0.076 |

Wells coated with LAL captured LPS from gonococcal organisms, retained the LPS through the washing steps, and presented it in a form that was antigenically intact and accessible to gonococal LPS-specific monoclonal antibody for a sandwich assay. The amount of LPS antigen captured increased with increasing concentrations of LAL adsorbed to the wells.

EXAMPLE 2

Sandwich Assay for *Escherichia Coli* LPS

Lipopolysaccharide purified from *Escherichia coli* strain K235 was purchased from List Biologicals. Lyophilized Limulus amebocyte lysate (Pyrogent) was reconstituted in sterile distilled water to a concentration of 5.4 mg/mL, was divided into 0.39-mL aliquots, and frozen at −20° C. until needed. Immediately before use, the LAL was thawed and 8 mL of LPS-free PBS was added to a concentration of 250 µg LAL/mL.

To different wells of a microtiter plate were added 100 µL of LAL and the plate was allowed to stand for 2 hours at room temperature. The plate was washed six times with PBS. The wells were then blocked with 200 µL of 0.5% (w/v) BSA in PBS and the plate was allowed to stand at room temperature for 1 hour. The plate was again washed 6 times with PBS. The LAL-coated wells were contacted with LPS from *E. coli* K235 (10, 50, and 250 ng per well, respectively) for 1 hour at room temperature. The plate was again washed 6 times with PBS. All wells then received 100 µL of rabbit anti-*E. coli* K235 LPS (diluted 1/100 in 0.1% BSA in PBS) and were allowed to stand for 1 hour at room temperature. The plate was washed 6 times with PBS. Each well then received 100 µL of a solution of a horseradish peroxidase-protein-A conjugate diluted 1:2000 in 0.1% BSA in PBS. This was allowed to stand for 1 hour at room temperature. The plate was washed 6 times with PBS, then 100 µL of freshly prepared chromogenic substrate, 1.5 µM TMB solution, was added to all wells. The optical density of the substrate solution was read at 630 nm after 10 minutes using an MR-600 microtiter plate reader with the reference beam set to 490 nm. The results are presented in Table 2.

TABLE 2

| DETECTION OF *E. COLI* LPS | |
| --- | --- |
| ng of LPS | Optical Density (at 630 nm) |
| 0 | 0.007 ± 0.002 |
| 10 | 0.045 ± 0.006 |
| 50 | 0.190 ± 0.004 |
| 250 | 0.403 ± 0.023 |

This example shows that *E. coli* K235 LPS can be captured by immobilized LAL and as little as 10 ng of LPS in the sample detected immunologically in a sandwich assay using specific antibody. The sensitivity of the assay was especially surprising because no assay optimization had been carried out and, also, unpurified polyclonal rabbit antiserum was utilized.

EXAMPLE 3

Sandwich Assay for Gonococcal LPS from Different Strains

Nine strains of *N. gonorrhoeae*, differing in serotype specificity, were grown, harvested, and heat inactivated as described in Example 1. The bacterial suspensions were adjusted to a concentration of $1 \times 10^6$ CFU/mL. An aliquot of LAL from Example 2 was thawed, adjusted to 215 µg/mL in PBS, and 100 µL was placed in the wells of a microtiter plate. The plate was allowed to stand at room temperature for 2 hours and then washed 6 times in PBS. Each well then received 200 µL of 0.5% BSA in PBS and was allowed to stand for 1 hour at room temperature. The plate was again washed 6 times in PBS. Each well then received 100 µL of the different inactive gonococcal suspensions. For control, LPS-free PBS was used. The plate was allowed to stand for 1 hour at room temperature and then washed 6 times in PBS. The contents of the wells were then separately treated with either 100 µL of *N. gonorrhoeae*-specific monoclonal antibody [06B4 IgM class, described in R. Mandrell et al., Infection and Immunity, Volume 54, 63–69 (1986)] diluted 1/200 in 0.1% BSA or a mixture of two monoclonal antibodies, the mixture containing 50 µL of 06B4 diluted 1/100 and 50 µL of monclonal antibody 179 diluted 1/250 in 0.01% BSA. After incubating for 1 hour at room temperature, the wells were washed 6 times with PBS and then treated with 100 µL of protein-A horseradish peroxidase conjugate (Miles Laboratories). After incubation for 1 hour at room temperature, the plate was washed 6 times in PBS, and treated with 100 µL of freshly prepared 1.5 µM TMB solution. The absorbance at 630 nm was read after 10 minutes at room temperature using an MR-600 microtiter plate reader with the reference beam set to 490 nm.

In a separate experiment, LAL (236 µg/mL) was coated on wells of a microtiter plate and the same nine gonococal strains (serotypes 1–9) were incubated at high concentrations ($8 \times 10^7 - 1 \times 10^9$ CFU/mL) with the active support. After washing, a conjugate of antibody 179 with HRP was added to the cells followed by substrate. Optical density was determined as above at 630 nm. The results from these separate experiments are presented in Table 3.

TABLE 3

| DETECTION OF GONOCOCCAL SEROTYPES | | | |
| --- | --- | --- | --- |
| | Optical Density (at 630 nm)/Antibody | | |
| Serotype | 06B4 | 179 | 06B4 + 179 |
| blank | 0.025 | 0.025 | 0.067 |
| 1 | 0.041 | 0.037 | |
| 2 | 0.081 | 0.202 | |
| 3 | 0.019 | 0.000 | |
| 4 | 0.030 | 0.000 | |
| 5 | 0.051 | 1.005 | 0.281 |
| 6 | 0.129 | 0.368 | |
| 7 | 0.134 | 0.175 | |
| 8 | 0.074 | 0.365 | 0.173 |
| 9 | 0.091 | 0.926 | 0.377 |

As can be seen from the Table, antibody 06B4 reacts well, for example, with serotypes 6 and 7, while antibody 179 reacts strongly with serotypes 5, 8, and 9, but weakly or not at all, for example, with serotypes 2, 3, 4, and 7. Thus, this experiment demonstrates the feasibility of using multiple antibodies as detection reagents in order to broaden the specificity of the detection reagent; shows that LPS captured by LAL remains accessible even to large immunoglobulin molecules (06B4 is an IgM antibody); and that the method of this invention is capable of detecting various and large numbers of bacterial serotypes.

EXAMPLE 4

Effect of Reaction Temperature on Assay Performance

*N. gonorrhoeae*, serotype 5, was grown, harvested, and inactivated as described in Example 1. In this experiment, the assay procedure was altered to examine the effect of temperature at which the assay is performed on the LAL capture assay of this invention. Two separate microtiter plates were used. All steps were performed on one of the plates at room temperature and at 37° C. on the other plate. The plates were coated with 100 μL of LAL, 250 μg/mL in PBS, allowed to stand, then washed with PBS, blocked with 200 μL of 0.5% BSA in PBS, and washed again with PBS. Both plates then received 100 μL of various dilutions of heat killed gonococci (serotype 5), while control wells received 100 μL of PBS. One plate was allowed to stand at room temperature for 1 hour while the other, at 37° C. for 30 minutes. Both plates were washed 6 times with PBS and then received 100 μL of rabbit anti-*N. gonorrhoeae* polyclonal antibody, diluted 1/500 in 0.1% BSA. The plates were allowed to stand at room temperature for 1 hour and at 37° C. for 30 minutes, respectively. Both plates were washed, followed by the addition of 100 μL of a horseradish peroxidase-protein-A conjugate, diluted 1/2000, to all wells. Again, the plates were incubated as before, washed 6 times with PBS, followed by the addition of 100 μL of freshly prepared 1.5 μM TMB solution to all wells. The optical density at 630 nm was read after 10 minutes at room temperature (for both plates) using an MR-600 microtiter plate reader with the reference beam set to 4980 nm. The results are presented in Table 4. The signal/noise ratio is the ratio of absorbances in presence and absence of cells and is an indication of assay sensitivity.

TABLE 4
EFFECT OF TEMPERATURE

| No. of Cells | Incubation (°C./min) | Optical Density (at 630 nm) | Signal/ Noise |
|---|---|---|---|
| — | 25/60 | 0.019 ± 0.005 | — |
| $1 \times 10^3$ | 25/60 | 0.013 ± 0.003 | 0.7 |
| $5 \times 10^3$ | 25/60 | 0.015 ± 0.001 | 0.8 |
| $1 \times 10^4$ | 25/60 | 0.021 ± 0.004 | 1.1 |
| $5 \times 10^4$ | 25/60 | 0.048 ± 0.002 | 2.5 |
| $1 \times 10^5$ | 25/60 | 0.082 ± 0.002 | 4.3 |
| $1 \times 10^6$ | 25/60 | 0.274 ± 0.014 | 14.4 |
| $1 \times 10^7$ | 25/60 | 0.371 ± 0.013 | 19.5 |
| — | 37/30 | 0.004 ± 0.004 | — |
| $1 \times 10^3$ | 37/30 | 0.029 ± 0.007 | 7.3 |
| $5 \times 10^3$ | 37/30 | 0.045 ± 0.019 | 11.2 |
| $1 \times 10^4$ | 37/30 | 0.030 ± 0.010 | 7.5 |
| $5 \times 10^4$ | 37/30 | 0.091 ± 0.007 | 22.8 |
| $1 \times 10^5$ | 37/30 | 0.177 ± 0.016 | 44.3 |
| $1 \times 10^6$ | 37/30 | 0.796 ± 0.055 | 199.0 |
| $1 \times 10^7$ | 37/30 | 1.179 ± 0.037 | 294.8 |

Performing the incubation steps in the sandwich assay of this invention for 30 minutes at 37° C. instead of room temperature for 1 hour greatly improved assay sensitivity and also shortened the time needed to carry out the assay. At 25° C., $5 \times 10^4$ cells were required in order to achieve a signal to noise ratio greater than 2, while at 37° C., as low as $1 \times 10^3$ cells gave a signal to noise ratio of more than 7, a 50-fold increase in sensitivity.

EXAMPLE 5

Sequential, Staggered and Simultaneous Assay

In this Example, various reagent addition sequences were examined: the sequential, staggered and simultaneous methods of carrying out the sandwich assay of this invention.

The wells of microtiter plates were coated with LAL (250 μg/mL, Example 2) and allowed to stand for 2 hours at 37° C. The wells were then washed 6 times with PBS and blocked with 200 μL of 0.5% BSA in PBS (1 hour, 37° C.). Rabbit polyclonal anti-*N. gonorrhoeae* antibody was used as the detection reagent.

The sequential addition method has been described in Examples 1–4. A suspension of heat killed gonococcal cells (50 μL, $5 \times 10^6$ cells) was added to wells along with 50 μL of PBS. This was incubated (30 min, 37° C.) and then washed 6 times with PBS. The LAL-LPS complexes so formed were treated with 100 μL of antiserum (diluted 1/500) in each well and were incubated at 37° C. for 30 minutes. Antibody binding was measured by using an HRP-protein-A conjugate according to the procedure used in Example 4.

The simultaneous addition method was performed by adding both the gonococcal cell suspension ($5 \times 10^6$ cells) and antibody (100 μL, 1/500 dilution) to the LAL-coated wells (the active support) at the same time. After incubation at 37° C. for 30 minutes, the plates were washed 6 times with PBS and antibody binding was measured by using the HRP-protein-A conjugate as described above.

The staggered addition assay was performed by adding the gonococcal cell suspension ($5 \times 10^6$ cells) to the LAL-coated wells, incubating for 15 minutes at 37° C., and then adding the antibody (100 μL, 1/500 dilution) without performing a separation/wash step prior to antibody addition. After incubation for another 15 minutes at 37° C., the wells were washed 6 times with PBS and antibody binding was measured using the HRP-protein-A conjugate as described above.

Control wells for each method were treated as the test wells except that PBS was added instead of gonococcal cells. The results are reported in Table 5.

TABLE 5
SANDWICH ASSAY PROCEDURES

| Reagent Addition | Sample | Optical Density (at 630 nm) | Signal/ Noise |
|---|---|---|---|
| Sequential | Control | 0.011 ± 0.001 | — |
|  | Cells | 0.313 ± 0.009 | 28.5 |
| Simultaneous | Control | 0.024 ± 0.001 | — |
|  | Cells | 0.167 ± 0.007 | 7.0 |
| Staggered | Control | 0.017 ± 0.002 | — |
|  | Cells | 0.205 ± 0.007 | 12.1 |

These results show that the sequential procedures provided the best performance with respect to both the total signal generated and the signal to noise ratio. Assay time could be shortened by combining various steps of the assay with a concomitant reduction of assay performance. The staggered procedure improved the total signal and the signal to noise ratio over the simultaneous procedure. The latter addition gave 47.4% of the specific signal (difference between absorbance values for wells with cells and the control) of the sequential addition, whereas staggered addition gave 62.3% of the specific signal.

What is claimed is:

1. A sandwich assay for detecting lipopolysaccharides comprising the steps of:
   (A) immobilizing a specific, non-immunochemical capture reagent in a substantially surfactant-free environment below pH=9 to form an active support consisting essentially of
   (i) a water insoluble support; and
   (ii) lipopolysaccharide binding proteins of amebocyte lysates bound to said support;

(B) contacting a substantially surfactant-free sample containing or suspected of containing lipopolysaccaharides with said active support;

(C) contacting the active support-LPS complex formed in step (B) with a substantially surfactant-free labelled detection reagent; and (D) detecting either the bound or unbound label.

2. The sandwich assay of claim 1 wherein the lipopolysaccharide binding proteins are selected from the binding proteins of the amebocyte lysates consisting of *Limulus polyphemus, Tachypleus tridentatus, Carcinoscorpius rotundicauda* and *Tachypleus gigas*.

3. The sandwich assay of claim 1 wherein the complex formed in step (B) is separated from any unbound material.

4. The sandwich assay of claim 1 wherein the active support is contacted substantially simultaneously with the sample and the labelled detection reagent.

5. The sandwich assay of claim 1 wherein the labelled detection reagent is a conjugate of a specific binding protein for lipopolysaccharides and a label.

6. The sandwich assay of claim 5 wherein the specific binding protein is selected from the group consisting of immunoglobulins, lectins and pure lipopolysaccharide binding proteins.

7. The sandwich assay of claim 5 wherein the label is selected from the group consisting of radioisotopes, enzymes and fluorescent molecules.

8. A method for removing lipopolysaccharides from a sample comprising the steps of:

(A) immobilizing a specific, non-immunochemical capture reagent in a substantially surfactant-free environment below pH=9 to form an active support consisting essentially of
  (i) a water insoluble support; and
  (ii) lipopolysaccharide binding proteins of amebocyte lysates bound to said support;

(B) contacting a substantially surfactant-free sample containing or suspected of containing the lipopolysaccharide with the active support; and (C) separating the LPS bound to the active support from the sample.

* * * * *